United States Patent
Kishida et al.

(10) Patent No.: US 6,242,565 B1
(45) Date of Patent: *Jun. 5, 2001

(54) METHOD FOR PREPARING A PEPTIDE DERIVATIVE, AND INTERMEDIATES FOR THE PREPARATION OF THE PEPTIDE DERIVATIVE, AND METHOD FOR PREPARING THE INTERMEDIATES

(75) Inventors: Satoshi Kishida; Akihiro Nakanishi; Hitoshi Kimura, all of Ibaraki (JP)

(73) Assignee: TT Pharmaceuticals, Inc., Tokyo (JP)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/129,644

(22) Filed: Aug. 5, 1998

(30) Foreign Application Priority Data

Aug. 8, 1997 (EP) .................................................. 97306070

(51) Int. Cl.$^7$ .............................. C02K 5/00; C02K 7/00; C02K 16/00; C02K 17/00
(52) U.S. Cl. ....................... 530/333; 530/328; 530/335; 530/336; 530/338; 530/339
(58) Field of Search ................................. 530/328, 333, 530/335, 336, 338, 339

(56) References Cited

U.S. PATENT DOCUMENTS

| 4,719,199 | 1/1988 | Yim | 514/9 |
| 5,373,089 | * 12/1994 | Flouret et al. | 530/315 |
| 5,596,078 | * 1/1997 | Andersson et al. | 530/315 |
| 5,712,418 | * 1/1998 | Carpino et al. | 564/225 |

FOREIGN PATENT DOCUMENTS

WO 94/25485  11/1994  (WO).

OTHER PUBLICATIONS

Manning, M. et al: "Effects of a D–Cys6/L–Cys6 Interchange in Nonselective and Selective Vasopressin and Oxytocin Antagonists", J. Med. Chem., vol. 38, 1995, pp. 1762–1769; XP002049528.

* cited by examiner

Primary Examiner—Dwayne C. Jones
Assistant Examiner—C. Delacroix-Muirheto
(74) Attorney, Agent, or Firm—Nixon & Vanderhye P.C.

(57) ABSTRACT

A method for preparing a peptide derivative of formula (I) or a salt thereof:

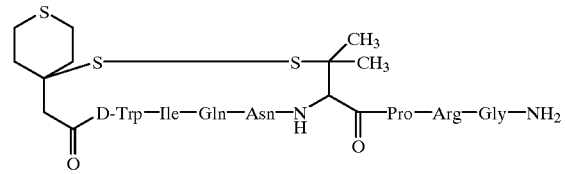

(I)

which method comprises the steps of removing two MBzl groups from a compound of formula (II) or a salt thereof:

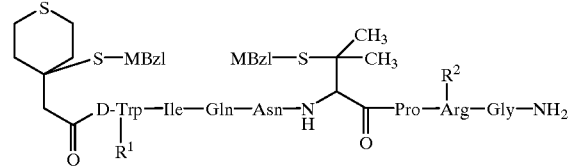

(II)

wherein MBzl represents a 4-methoxybenzyl group which serves as a protective group for a thiol group, and $R^1$ and $R^2$ represent hydrogen or a protective group for Trp or Arg respectively; and subsequently oxidizing in an aqueous medium having a pH from 4 to 6 to form an intramolecular disulphide bond; intermediates useful for preparing the compounds of formula (I) and preparation of the intermediates.

6 Claims, 1 Drawing Sheet

METHOD FOR PREPARING A PEPTIDE DERIVATIVE, AND INTERMEDIATES FOR THE PREPARATION OF THE PEPTIDE DERIVATIVE, AND METHOD FOR PREPARING THE INTERMEDIATES

The present invention relates to a method for preparing a peptide derivative having physiological activities, and more particularly to a method for preparing a peptide derivative which is useful for the prevention of early abortion and which exhibits anti-oxytocin activities while exhibiting reduced anti-vasopressin activities. The invention also relates to intermediates useful in the method, as well as to the method for preparing the intermediates.

Pre-full-term delivery is one of the most serious problems in obstetrics. Many pregnant women who have passed 20 weeks of gestation have experienced premature births and immature deliveries, which together constitute the primary cause of neonatal diseases and neonatal deaths. Therefore, even today, when neonatal treatment is greatly advanced, the consensus opinion is that the fetus is preferably carried by its mother's body until the month of expected delivery.

Uterine muscle relaxants are generally used for the treatment of pre-full-term delivery. In recent years, oxytocin antagonists have been proposed as ideal uterine muscle relaxants for suppressing pre-full-term delivery. This proposal was based on the finding that oxytocin, a peptide hormone, is a physiological parturifacient. Further research led to the finding of a novel oxytocin receptor antagonist which is a peptide derivative of the following formula (I):

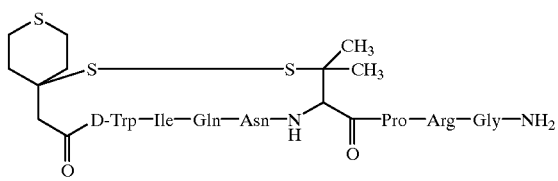

(I)

and which is disclosed in International Patent Publication WO94/25485.

Oxytocin, a posterior pituitary hormone, is composed of nine amino acid residues. Vasopressin, another posterior pituitary hormone, is also composed of nine amino acid residues, which with the exception of two amino acid residues are identical to those of oxytocin. These two substances, notwithstanding their similar structures, exhibit very different physiological activities; oxytocin functions to constrict smooth muscles including uterine muscle, whereas vasopressin exhibits peripheral vasoconstriction and elevation of blood pressure. Thus, anti-oxytocin drugs previously developed often exhibit a side effect of anti-vasopressin activity.

However, the aforementioned peptide derivative of formula (I) are considered to be ideal uterine muscle relaxants, because the derivatives function as potent oxytocin receptor antagonists while they never exhibit vasopressin antagonizing activity, which is a side effect exerted by conventional oxytocin receptor antagonists.

WO94/25485 referred to hereinabove discloses a method for preparing the compounds of formula (I). According to that publication, the peptide derivatives are prepared by use of a so-called solid phase method in which a resin carrier is employed. Mass-production of the compounds of formula (I) at high purity and high yield is difficult to achieve by the solid phase method.

For example, as experienced with commercially available automatic peptide synthesizers, which automatically synthesize peptides making use of the solid phase method, the process steps are lengthy, because amino acids are sequentially bonded to the resin carrier in a one-by-one manner through condensation reaction. It is also noted that in each step, post-condensation purification cannot be performed, and inclusion of peptides that lack portions of amino acids cannot be prevented. In order to reduce the occurrence of such defective peptides, condensation reaction is performed by use of an excessive amount of an amino acid derivative, i.e., 2 to 6 times that of the amino group content of peptide joined to the carrier resin. However, under general circumstances, prevention of the occurrence of defective peptides by such an approach is difficult.

It is also noted that in a step in which a required peptide moiety is separated from the carrier resin, contamination is caused by the side reaction products on the cleavage of peptide resins and also by impurities such as defective peptides that lack one or more amino acids, the defective peptides being formed because the intermediate cannot be purified in the course of reaction. Therefore, an intricate purification process must be performed to obtain the target compound having a high level of purity.

Moreover, according to the above-mentioned publication, the target peptide is separated from the carrier resin by use of a liquid ammonia solution in which sodium metal is dissolved, and such a method is industrially difficult to perform.

In the field of peptide synthesis, many methods have been disclosed for forming intramolecular SS bonds ("Development of Pharmaceuticals, Second Series" Vol. 14, 'Peptide Synthesis' pp. 233–258, 1991, Hirokawa Shoten). Among such methods, when potassium ferricyanide is used, the reaction is usually performed in the vicinity of neutral pH, i.e., between 6.0 and 8.0 (Chem. Pharm. Bull., Vol. 38, page 1920, 1990). However, under this reaction condition, intermolecular SS bonds are formed in much greater numbers than are intramolecular SS bonds or intramolecular cyclization, and therefore, the target compound cannot be obtained at high yield.

In addition, according to the method disclosed in the aforementioned publication WO94/25485, the intermediate used in the synthesis of the formula (I) compound is a compound in which the protective group for thiol is 4-methylbenzyl. Accordingly, when an intramolecular SS bond (disulfide bond) is formed, great care must be taken so as to assure safety, etc., because liquid ammonia solution in which metallic sodium has been dissolved is employed for removing the protective group.

Accordingly, the general object of the present invention is to provide a compound of formula (I) at high yield and a high level of purity in an industrially efficient manner.

The present inventors have conducted extensive studies on methods for preparing peptide derivatives of formula (I), and have successfully established a synthesis scheme which is not dependent on the solid phase method and is suited to the liquid phase method, and have found that the above-mentioned general object can be achieved by use of a certain intermediate, which is cyclized via the formation of intramolecular SS bonds through a specific process, thus leading to completion of the present invention.

The present invention provides a method for preparing a peptide derivative of formula (I) or a salt thereof:

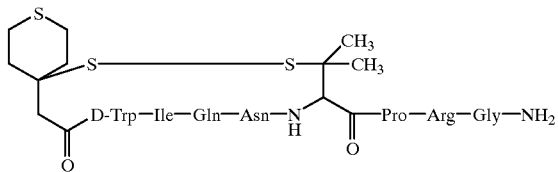

(I)

which method comprises the steps of removing two MBzl groups from a compound of formula (II) or a salt thereof

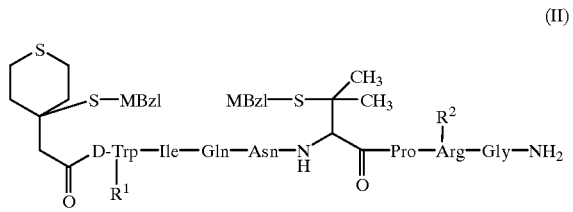

(II)

wherein MBzl represents a 4-methoxybenzyl group which serves as a protective group for a thiol group, R¹ represents a hydrogen atom or a protective group for the indolyl group of D-Trp and R² represents a hydrogen atom or a protective group for the guanidino group of Arg, and subsequently oxidizing in an aqueous medium having a pH from 4 to 6 to form an intramolecular disulphide (SS) bond.

The present invention also provides a compound of formula (II) or a salt thereof as described above, which serves as an intermediate in the synthesis of the formula (I) compound.

The present invention further provides a method for preparing a compound of formula (III) or a salt thereof: wherein R¹ represents a hydrogen atom or a protective group for the indolyl group of D-Trp, R² represents a

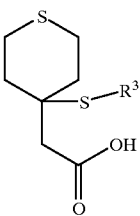

(XI)

wherein R³ is a protective group for thiol to obtain a compound of formula (III) or a salt thereof.

In addition, the present invention provides a compound of formula (III) or a salt thereof as described above, which serves as an intermediate in the synthesis of formula (I) compound.

Figure 1:
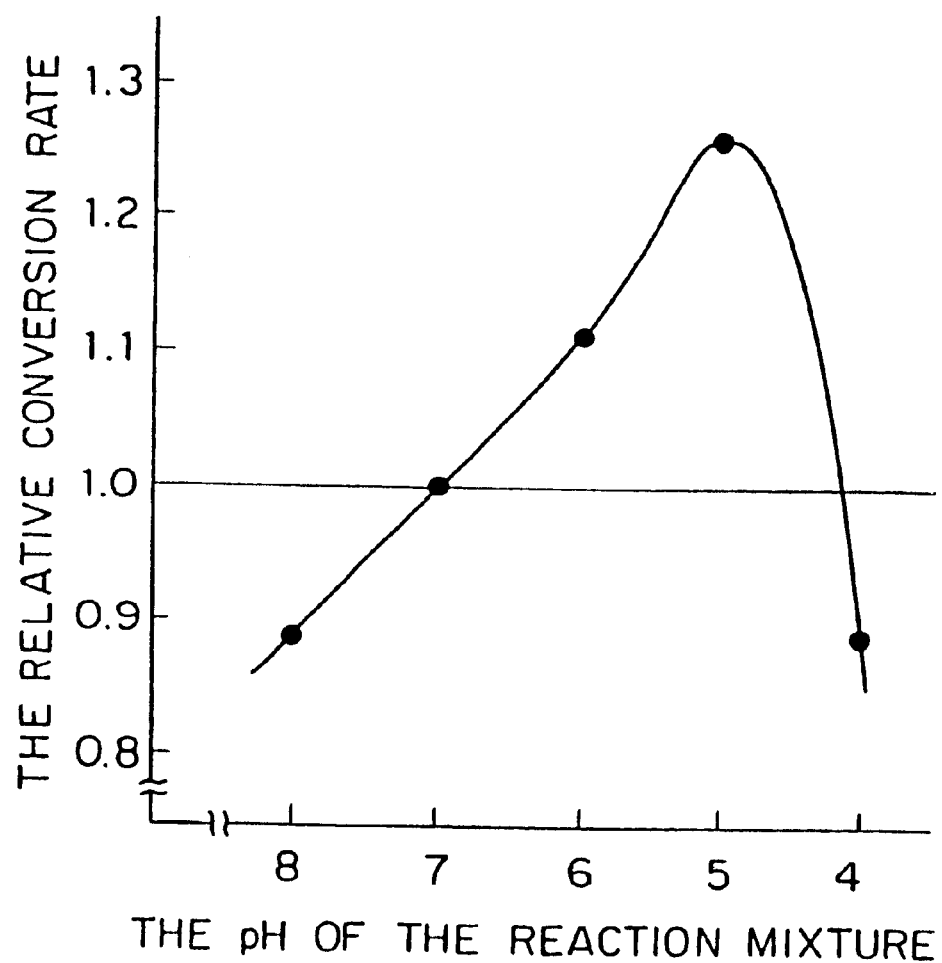
FIG. 1 is a graph showing the effect of pH on the formation of intramolecular SS bonds.

Abbreviations used throughout the present specification are listed below.
Optical Isomers:

In the case where the amino acids or other compounds used in the present invention have optical isomers, when D-type compounds are used, "D-" is placed before the words representing such amino acids or compounds (e.g. D-Trp is D-tryptophan). Unless explicitly indicated otherwise, L-type compounds are meant.
Amino Acid Residues:

Arg: arginine, Asn: asparagine, Ile: Isoleucine, Gln: glutamine, Gly: glycine, Pro: proline, Trp: tryptophan
Protective Groups:

Acm: acetamidemethyl, Boc: t-butoxycarbonyl, Z: benzyloxycarbonyl, Cl-Z: 2-chlorobenzyloxycarbonyl, Br-Z: 2-bromobenzyloxycarbonyl, Fmoc: 9-fluorenylmethoxycarbonyl, Bzl: benzyl, MBzl: 4-methoxybenzyl, Tos: tosyl, Mts: 2,4,6-trimethylbenzenesulfonyl, Mtr: 4-methoxy-2,3,6-trimethylbenzenesulfonyl, Pmc: 2,2,5,7,8-pentamethylchroman-6-sulfonyl, Pbf: 2,2,4,6,7-pentamethyldihydrobenzofuran-5-sulfonyl.
Dehydration Condensation Coupling Reagents:

HOBt: 1-hydroxybenzotriazole, HOSu: N-hydroxysuccinimide, HOOBt: 3-hydroxy-3,4-dihydro-4-oxo-1,2,3-benzotriazine

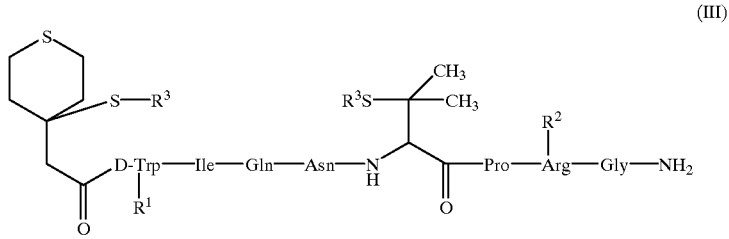

(III)

hydrogen atom or a protective group for the guanidino group of Arg, and R³ is a protective group for a thiol group; which method comprises reacting a compound of formula (Xa) or a salt thereof:

wherein R¹, R² and R³ are as defined above; with a compound of formula (XI):

Solvents:

DOX: dioxane, DMF: dimethylformamide, TFA: trifluoroacetic acid, NMP: N-methylpyrrolidone, THF: tetrahydrofuran
Removal of a Protective Group:

In the present invention, protective groups may be removed by customary methods used in the field of peptide synthesis.

Examples of usable customary methods include a catalytic hydrogenation method, a method performed under strongly basic conditions and making use of ammonia compounds or hydrazine, a method performed under acidic conditions and making use of TFA, hydrogen fluoride, or trifluoromethanesulfonic acid, and a method making use of iodine. In the method in which TFA is used, TFA may be used singly. Alternatively, mixtures of TFA and mercaptanes or phenols may be used, or methanesulfonic acid may also be added to the resultant mixtures.

Dehydration Condensation:

According to the present invention, dehydration condensation of the individual peptide derivatives or amino acids may be performed through customary methods for synthesizing peptides.

Examples of such methods include C-terminal activation methods such as active ester methods and symmetric acid anhydride methods, and coupling methods in which coupling reagents are used.

(1) Illustrative examples of active esters usable in the active ester methods include alkyl esters such as cyanomethylester; phenyl esters such as thiophenyl esters, p-nitrophenyl thioesters, p-methanesulfonyl phenyl esters, p-nitrophenyl esters, 2,4-dinitrophenyl esters, 2,4,6-trichlorophenyl esters, and pentachlorophenyl esters; dicarboxylic imide esters such as N-hydroxysuccinimide esters, N-hydroxyphthalimide esters, and N-hydroxy-5-norbornane-2,3-dicarboxylimide (HONB); and hydroxyamine derivatives such as 8-hydroquinoline esters, N-hydroxypiperidine esters, and 2-hydroxypyridine esters.

(2) Examples of coupling methods include the carbodiimide method making use of dicyclohexylcarbodiimide (DCC), water-soluble carbodiimide (WSC), etc.; DCC-additive method; carbodiimidazole (CDI) method; Woodward method in which are employed isooxazolium salts such as N-ethyl-5-phenylisooxazolium-3'-sulfonates and N-ethyl-2'-hydroxybenzisooxazolium trifluoroborate, 1-ethoxycarbonyl-2-ethoxy-1,2-dihydroxyquinoline (EEDQ), 1-ethoxycarbonyl-2-isobutoxy-1-yl-oxytris(dimethylamino)phosphonium-hexafluorophosphate (BOP), O-benzotriazole-N,N,N',N'-tetramethyluronium hexafluorophosphate (HBTU), or diphenylphosphorylazide (DPPA); oxidation-reduction method according to Mukaiyama et al., and 4-component synthesis method (Ugi method).

(3) Examples of WSC include 1-ethyl-3-(3-diethylaminopropyl)carbodiimide (EDC), N-cyclohexyl-N'-morpholinoethylcarbodiimide, and N-cyclohexyl-N'-(N,N-diethylamino)cyclohexylcarbodiimide. WSCs may be in the form of salts such as hydrochlorides.

(4) Examples of DCC-additive methods include the DCC-HOSU method, DCC-HOBt method, DCC-HOOBt method, DCC-HONB method, DCC-2-hydroxyimino-2-cyanoacetic acid ester method, WSC-HOSU method, WSC-HOBt method, and WSC-HOOBt method.

Addition Salts and Complexes:

The active peptide derivatives, their intermediates, and starting materials according to the present invention may take, and preferably take, the form of acid addition salts or complexes (hereinafter simply referred to as salts), if such can be formed. When salts are not pharmaceutically accepted, they can be transformed into pharmaceutically acceptable salts.

Examples of acid addition salts include salts of inorganic acids such as hydrochloric acid, sulfuric acid, hydrobromic acid, and phosphoric acid; and salts of organic acids such as formic acid, acetic acid, TFA, propionic acid, glycolic acid, lactic acid, pyruvic acid, oxalic acid, succinic acid, malic acid, tartaric acid, citric acid, benzoic acid, salicylic acid, benzenesulfonic acid, and toluenesulfonic acid.

Examples of complexes include inorganic compounds derived from metals such as calcium, magnesium, aluminum, cobalt, and zinc. Particularly, mention may be given to slightly soluble salts such as phosphoric acid salts, pyrophosphoric acid salts, polyphosphoric acid salts, etc. of these metals, as well as hydroxides of these metals and polyphosphates of alkali metals. As used herein, the compounds encompass salts thereof unless specifically indicated.

Next, steps for the preparation of an intermediate of formula (III) to a compound of formula (I) are described in this order.

Method for Preparing a Compound of Formula (III)

A compound of formula (III) (hereinafter may be referred to as compound (III), and the same rule for naming is applied to other compounds) is prepared through a backbone synthesis method making use of fragment condensation. Briefly, the below-described compounds (IV), (VII), and (V), all of which are tripeptide derivatives, are prepared in advance by synthesis, etc., and these compounds are sequentially bonded to each other. This method is advantageous in that occurrence of deficient amino acids is reduced, and the yield of compound (III) can be raised.

In the present invention, compound (VII) and a penicillamine derivative, compound (VI), are subjected to a condensation reaction. The reason why this reaction is introduced is that compound (V) is predicted to undergo condensation reaction slowly due to its steric hinderance, etc., and it is considered that reaction proceeds at higher yield when compound (IV) which has been synthesized in advance is first reacted with compound (V), and subsequently with compound (VII), and in addition, compound (VII) plays a useful part in the fragment condensation because compound (VII) can be isolated and recovered as a pure substance by recrystallization. Subsequently, D-Trp derivative, compound (IX) is subjected to a condensation reaction. This step is also for the purpose of reducing the frequency of reactions that involve the risk of occurrence of adverse side reaction. Finally, when compound (XI) is reacted for condensation, compound (III) is obtained.

Starting Materials:

a. Compound (IV)

$$R^4\text{-Pro-Arg}(\text{-}R^2)\text{-Gly-NH}_2 \qquad (IV)$$

wherein $R^2$ is a hydrogen atom or a protective group for a guanidino group, and $R^4$ is a protective group for the imino group of Pro.

In Compound (IV), when $R^2$ is a protective group for guanidino, $R^2$ is preferably a nitro group or a group Z. In the present invention, $R^2$ is most preferably a hydrogen atom. $R^4$ is preferably Z, Boc, or Fmoc.

Compound (IV) may be prepared through a routine peptide synthesis method. For example, a hydrochloric acid salt of glycinamide is subjected to a condensation reaction with arginine whose amino and guanidino groups are protected, to thereby form a dipeptide derivative, and subsequently, the protective group for the amino group of arginine is removed. Thereafter, proline having protected imino is reacted for condensation. Alternatively, a dipeptide derivative may be formed through condensation with arginine in which only the amino group is protected, and subsequently, the protective group for the amino group of arginine may be removed, and then proline having protected imino may be reacted for condensation.

b. Compound (V)

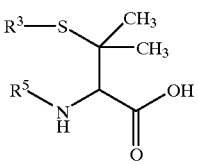
(V)

wherein $R^3$ represents a protective group for a thiol group and $R^5$ represents a protective group for an amino group.

In the above formula, $R^3$ is preferably a MBzl group, 4-methylbenzyl group, or an Acm group; more particularly a MBzl group. The amino protective group $R^5$ is preferably Boc or Fmoc.

c. Compound (VII)

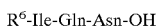
$R^6$-Ile-Gln-Asn-OH (VII)

wherein $R^6$ represents a protective group for the amino group of Ile.

Similar to the aforementioned compound (IV), compound (VII) may be prepared through a conventional method for synthesizing peptides.

d. Compound (IX)

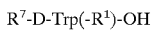
$R^7$-D-Trp(-$R^1$)-OH (IX)

wherein $R^1$ represents a hydrogen atom or a protective group for indolyl and $R^7$ represents a protective group for the amino group that is linked to the alpha carbon of D-Trp.

When $R^1$ is a protective group for the indolyl group of D-Trp, $R^1$ is preferably a formyl group or a Mtr group, more preferably a formyl group. $R^7$ is preferably Boc or Fmoc.

e. Compound (XI)

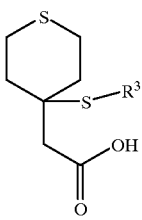
(XI)

wherein $R^3$ represents a protective group for thiol.

The protective group $R^3$ for the thiol group of compound (XI) is the same as the protective group $R^1$ of compound (V). Compound (XI) can be prepared through customary organic synthetic methods.

Process for the Preparation:

First, the protective group $R^4$ of the imino group of Pro of compound (IV) is removed. In the case where $R^4$ is Z, $R^4$ can be removed as follows. A hydrochloric acid salt of compound (IV) is dissolved in a solvent such as methanol, dimethylformamide, ethanol, or in an aqueous solution of such a solvent. The resultant solution is stirred in a hydrogen stream in the presence of Pd/C or palladium black. This process is a so-called catalytic hydrogenation. When the catalyst is removed by filtration and the solvent is evaporated, a hydrochloric acid salt of a compound (IV) from which the protective group $R^4$ has been removed can be obtained.

Next, the resultant compound (i.e., the hydrochloric acid salt of a compound (IV) from which the protective group $R^4$ has been removed) and compound (V) are subjected to a condensation reaction. Among the various methods listed hereinabove, preferred condensation reactions are the DCC-HOBt method, DCC-HOOBt method, WSC-HOBt method, or WSC-HOOBt method. When the DCC-HOBt method is used, the hydrochloric acid salt of a compound (IV) from which the protective group $R^4$ has been removed is dissolved in DMF, and to the solution are added 1.0–1.5 times as many mols of compound (V) and 1.0–1.5 times as many mols of HOBt. While the temperature of the resultant mixture is maintained between −10 and 30° C., more preferably between 0 and 10° C., 1.0–1.3 times as many mols of DCC are added, and the mixture is stirred for 8–36 hours between 0° C. and room temperature. After completion of the reaction, insoluble matter is removed by filtration, and the filtrate is concentrated to thereby obtain a hydrochloric acid salt of compound (VI).

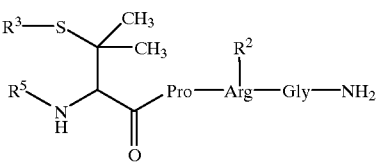
(VI)

wherein $R^2$ represents a hydrogen atom or a protective group for guanidino, $R^3$ represents a protective group for thiol, and $R^5$ represents a protective group for amino.

Subsequently, the protective group $R^5$ of compound (VI) is removed.

When $R^5$ is Boc, $R^5$ may be removed by dissolving compound (VI) in TFA at a temperature not higher than 30° C. and stirring for 30 minutes to 3 hours. TFA is then evaporated under reduced pressure, and the reaction is treated with DOX in which HCl gas, for example, has been dissolved. As a result, the TFA salt that has been produced is transformed into a hydrochloric acid salt, to thereby obtain a hydrochloric acid salt of a compound (VI) from which the protective group $R^5$ has been removed.

Next, the resultant compound (i.e., the hydrochloric acid salt of a compound (IV) from which the protective group $R^5$ has been removed) and compound (VII) are subjected to a condensation reaction. Among the various methods listed hereinabove, preferred condensation reactions are the WSC-HOOBt method, WSC-HOBt method, or DCC-HOBt method.

When the WSC-HOOBt method is used, the hydrochloric acid salt of a compound (VI) from which the protective group $R^5$ has been removed is dissolved in NMP or DMF. The pH of the solution is adjusted to between 7.0 and 9.0. To the solution are added 1.0–1.2 times as many mols of compound (VII) and 1.0–1.4 times as many mols of HOOBt. While the temperature of the resultant mixture is maintained between −20 and 20° C., more preferably between −20 and −10° C., 1.0–1.4 times as many mols of a hydrochloric acid salt of WSC is added, and the mixture is stirred for 8–36 hours in the same temperature range. When the reaction is performed in the above temperature ranges, racemization of the Asn residue of compound (VII) can be prevented. After completion of the reaction, insoluble matter is removed by filtration, and the filtrate is concentrated to thereby obtain a hydrochloric acid salt of compound (VIII).

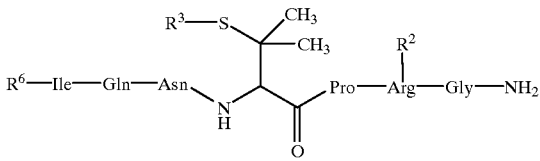

(VIII)

wherein $R^2$ represents a hydrogen atom or a protective group for guanidino, $R^3$ represents a protective group for thiol, and $R^6$ represents a protective group for the amino group of Ile.

Subsequently, the protective group $R^6$ is removed from compound (VIII).

$R^6$ may be moved by a method similar to that used for removing protective group $R^5$ from compound (VI).

Next, the resultant compound (i.e., a compound (VIII) from which the protective group $R^6$ has been removed) and compound (IX) are subjected to a condensation reaction. Among the various condensation methods listed hereinabove, preferred ones are the DCC-HOBt method or WSC-HOBt method. In particular, the DCC-HOBt method is preferred. When the DCC-HOBt method is used, the following method may be performed: a compound (VIII) from which the protective group $R^6$ has been removed is dissolved in DMF. The pH of the solution is adjusted to between 7.0 and 9.0. The subsequent reactions may be similar to those described for the condensation of compounds (IV) and (V). When DCC is added, the temperature of the reaction is preferably between −10 and 5° C.

The process of the present invention for synthesizing compound (X) is characterized in that compound (VI) is first bonded to $R^6$-Ile-Gln-Asn-OH (compound (VII)) and subsequently to $R^7$-D-Trp(-$R^1$)-OH (compound (IX)). This process must be distinguished from the process that $R^7$-D-Trp(-$R^1$)-Ile-Gln-Asn-OH, which is a condensate of compound (VII) and compound (IX), is synthesized in advance and then bonded to compound (VI). According to the present invention, since compound (VI) and compound (VII) are bonded to each other in advance, side reaction of the D-Trp residue of compound (X) can be advantageously prevented. When insoluble matter that precipitates after reaction is discarded by filtration and the filtrate is concentrated, a hydrochloric acid salt of compound (X) can be obtained.

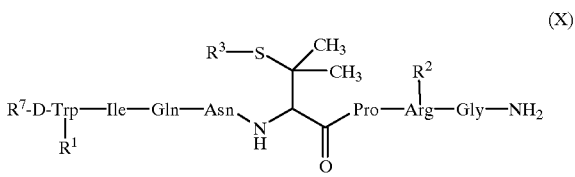

(X)

wherein $R^1$ represents a hydrogen atom or a protective group for indolyl, $R^2$ represents a hydrogen atom or a protective group for guanidino, $R^3$ represents a protective group for thiol, and $R^7$ represents a protective group for the amino group that is linked to the alpha carbon of D-Trp.

Subsequently, the protective group $R^7$ is removed from compound (X).

$R^7$ may be removed by a method similar to that used for removing protective group $R^5$ from compound (VI).

Finally, the resultant compound (i.e., a compound (X) from which the protective group $R^7$ has been removed) and compound (XI) are subjected to a condensation reaction. Among the various condensation reactions listed hereinabove, preferred ones are the DCC-HOBt method or WSC-HOBt method. The process is substantially the same as that described for the synthesis of compound (X) hereinabove. When insoluble matter that precipitates after reaction is discarded by filtration and the filtrate is concentrated, a hydrochloric acid salt of compound (II) can be obtained.

Method for Preparing a Compound of Formula (I)
(Starting Materials)

The compounds used in the method of the present invention for preparing compound (I) are compounds of formula (II), which are characterized in that the protective groups for their two thiol groups are both MBzl groups. Because of this feature, the two MBzl groups can be removed under the same conditions in a uniform manner. Moreover, since MBzl groups can be easily removed at low temperatures, side reactions of the D-Trp residue can be advantageously suppressed.

In formula (II), the protective group $R^1$ for the indolyl group of D-Trp is preferably formyl or Mtr, with formyl being more preferred due to its ease of removal. When $R^2$ is a protective group of the guanidino group of Arg, $R^2$ is preferably Z, Tos, nitro, or Mtr, with Z being more preferred. However, $R^2$ is particularly preferably a hydrogen atom. More specifically, in formula (II), $R^1$ and $R^2$ are preferably formyl and hydrogen, respectively. When $R^1$ is formyl, side reactions of a D-Trp residue can be suppressed when MBzl is removed under acidic conditions, in spite of the D-Trp residue's tendency to cause side reactions under acidic conditions. Moreover, when $R^2$ is a hydrogen atom, no procedure is required for removing the protective group for Arg. Also preferred are compounds of formula (II) in which $R^1$ and $R^2$ are both hydrogen atoms. In this case, the procedure of removing protective groups before and after the formation of intramolecular SS bonds is no longer required.

The method for preparing compound (II) is not limited to the above-described method for preparing compound (III). For example, amino acids may be sequentially added to the N-terminal side of a C-terminal amino acid, glycinamide, in a one-by-one manner. Alternatively, a hydrochloric acid salt of a compound (IV) from which a protective group $R^4$ has been removed may be subjected to a condensation reaction with the following compound (XII):

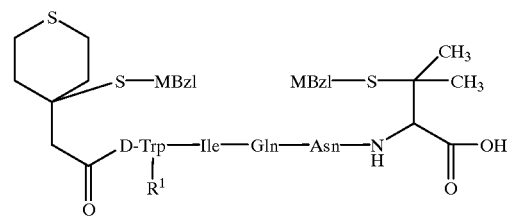

(XII)

wherein $R^1$ represents a hydrogen atom or a protective group for the indolyl group of D-Trp.

Process for the Preparation:

There are the following two processes in view of the removal of the protective group $R^1$ of compound (II) and sequence of the formation of intramolecular SS bonds.

(1) The protective groups other than protective group $R^1$ are removed. In other words, the two MBzl groups that protect the thiol groups and protective group $R^2$ are removed. Next, intramolecular SS bonds are formed through oxidation reaction. Subsequently, protective group $R^1$ is removed. This method can suppress side reactions which may otherwise occur to the Trp residue at the time of removing the protective groups other than $R^1$.

More specifically, if the MBzl group and protective group $R^2$ can be removed under acidic conditions, the MBzl group and protective group $R^2$ are both removed under acidic conditions, and the resultant dithiol is intramolecularly cyclized under acidic conditions. The same applies to the case in which $R^2$ is a hydrogen atom. The subsequent removal of protective group $R^1$ may be performed under acidic conditions or non-acidic conditions.

(2) After all protective groups in formula (II) are removed, intramolecular SS bonds are formed through oxidation reaction. The same applies to the case in which $R^1$ and $R^2$ are both hydrogen atoms. According to this method, no special procedure for removing $R^1$ is required, and simultaneous removal of the two MBzl groups suffices, thus making the reaction simple without raising fear of the occurrence of side reactions.

Removal of Protective Groups:

In order to remove the MBzl groups that serve as the protective groups for thiols while avoiding removal of protective groups $R^1$, the following method is preferred. Compound (II) is dissolved in 3–10 times the volume of TFA, to which m-cresol or similar substance is added as a scavenger in an amount of 0.02–1.0 times by mole that of TFA. Further, methanesulfonic acid is added in an amount of 0.02–0.3 time by mole. When the reaction is stirred for 30 minutes to 4 hours at a reaction temperature between 0 and 30° C., the protective groups for the two thiol groups can be removed simultaneously.

To remove protective group $R^2$ while leaving protective group $R^1$, catalytic hydrogenation may be performed when $R^2$ is Z, and a method making use of HF or trifluoromethanesulfonic acid may be used when $R^2$ is Tos. Also, when protective group $R^2$ is a nitro group, $R^2$ may be removed by use of liquid ammonia, whereas when $R^2$ is Mtr, $R^2$ may be removed by a method making use of TFA or TFA-thioanisole.

To remove protective group $R^1$ after formation of intramolecular SS bonds through oxidation reaction, if the protective group $R^1$ is a formyl group, $R^1$ can be removed by ammonia water, hydrazine, aqueous ammonium hydrogencarbonate solution, HF-ethanediol, or through a Low-High HF method. When protective group $R^1$ is Mtr, $R^1$ may be removed by a method making use of TFA or TFA-thioanisole. Particularly when $R^1$ is a formyl group, $R^1$ can be readily removed by the following procedure. A compound from which MBzl groups have been removed is dissolved in a large amount of buffer, e.g., ammonium acetate buffer that has been adjusted to pH 4.0–6.0. Potassium ferricyanide is added, and the resultant solution is stirred, to thereby form intramolecular SS bonds. Subsequently, the crude reaction mixture is treated with anion exchange resin or similar material so as to remove potassium ferricyanide. Without a concentration procedure being performed, conc. ammonia water is added to adjust the pH of the reaction mixture to fall in the range of 8.0–10.0, and the mixture is stirred for 2–48 hours at room temperature.

If protective group $R^1$ and MBzl groups are desired to be removed simultaneously, when $R^1$ is Mtr, the protective groups can be removed under the same conditions for removing MBzl groups. To remove protective group $R^1$, protective group $R^2$, and MBzl groups in a sequential manner, the aforementioned methods for removing these groups may be performed sequentially.

Formation of Intramolecular SS Bonds:

Intramolecular SS bonds are formed in an aqueous medium having a pH of 4.0–6.0. This pH range retards reaction of intramolecular SS bonds to thereby facilitate effective cyclization attributed to intramolecular SS bonds. pH may be controlled by use of ammonium acetate buffer, ammonium formate buffer, ammonium phosphate buffer, etc.

Intramolecular SS bonds may be formed by various methods including a method making use of air oxidation, a method in which air oxidation is effected in the co-presence of glutathione, and a method in which potassium ferricyanide is used as an oxidizer. In the present invention, it is preferable that potassium ferricyanide be used as an oxidizer and that the reaction be performed under weakly acidic conditions.

Potassium ferricyanide is preferably used in an amount of 1.0–2.0 times as many mols of compound (II). The concentration of potassium ferricyanide in the reaction mixture is preferably 0.005–0.1 wt. %. A concentration less than 0.005 wt. % makes the reaction rate extremely slow, whereas a concentration in excess of 0.1 wt. % permits the occurrence of intermolecular reaction, which greatly reduces the yield.

The concentration of compound (II) in the reaction mixture is preferably as low as 0.01–0.2 wt. %. A concentration less than 0.01 wt. % makes the reaction rate extremely slow, whereas a concentration in excess of 0.2 wt. % permits the occurrence of intermolecular reaction, which greatly reduces the yield. The reaction temperature is preferably between 15 and 40° C. from the viewpoint of mass production, and the reaction time is preferably between 0.5 and 48 hours.

Purification of Compound (I):

Compound (I) may be purified in accordance with conventional methods, making use of a variety of chromatography formats.

Examples of purification methods making use of chromatography include, but are not limited to, ion-exchange chromatography, gel filtration chromatography, reverse phase high performance liquid chromatography, affinity chromatography, reverse phase silica gel chromatography, and silica gel chromatography. Of these, preferred methods are ion-exchange chromatography, gel filtration chromatography, and reverse phase high performance chromatography, which may be suitably combined.

If desired, after being purified by any of the above-described methods, compound (I) may be subjected to a further purification process using a recrystallization method, reprecipitation method, etc.

EXAMPLES

The present invention will next be described by way of examples, which should not be construed as limiting the invention thereto. In the following examples, when compounds (1) through (11) form acid addition salts, the resultant salts are expressed as ".acid."

Synthesis Example 1:

Synthesis of Z-Pro-Arg-Gly-$NH_2$.HCl (Compound (1))

Z-Arg-OH (36.8 g; by Kokusan Kagaku K.K.) and H-Gly-$NH_2$.HCl (13.1 g; by Kokusan Kagaku K.K.) were suspended in DMF (200 ml). To the resultant suspension were added HOBt.$H_2O$ (18.3 g, by K.K. Peptide Kenkyusho) and DCC (24.5 g; by Kokusan Kagaku K.K.), and the mixture was stirred for 24 hours at room temperature. The precipitation was removed by filtration and the filtrate was concentrated and dried to thereby obtain an oily material. Ethyl acetate was added to the residue for solidification. The solidified materials were repeatedly washed with ethyl acetate and brought to complete dryness.

The entire amount of the obtained Z-Arg-Gly-NH$_2$.HCl was dissolved in 190 ml of methanol. 10 wt. % of Pd/C (4.8 g) was added to the solution. The mixture was then stirred in a hydrogen stream, to thereby remove the protective group. When the starting raw materials were completely undetected, the catalyst was discarded by filtration, and the filtrate was concentrated under reduced pressure.

The resultant oily material was dissolved in DMF (125 ml). To the resultant solution were added Z-Pro-OH (30.1 g, by Kokusan Kagaku K.K.), HOBt.H$_2$O (18.5 g), and DCC (25.5 g), and the mixture was stirred for 24 hours at room temperature. The precipitation was removed by filtration and the filtrate was concentrated under reduced pressure.

Ethyl acetate was added to the resultant oily material for solidification. The solidified substance was repeatedly washed with ethyl acetate and subsequently brought to dryness under reduced pressure, to thereby obtain 43.3 g of compound (1) (yield 73%).

Synthesis Example 2:

Synthesis of Boc-Ile-Gln-Asn-OH (Compound (4))

Boc-Ile-OH.1/2H$_2$O (41.1 g; by K.K. Peptide Kenkyusho) was dissolved in THF (191 ml). To the resultant solution were added HOSu (20.6 g, by Wako Pure Chemical Industries, Ltd.) and DCC (37.0 g), and the mixture was stirred for 20 hours at room temperature. The precipitation was removed by filtration and the filtrate was concentrated and brought to dryness. The residue was recrystallized with a mixture of isopropylether and isopropyl alcohol to thereby obtain 52.7 g of Boc-Ile-OSu.

Independently, glutamine (24.6 g; by K.K. Peptide Kenkyusho) was suspended in pure water (500 ml), and the suspension was dissolved by the addition of triethylamine. To the resultant solution was added the previously obtained Boc-Ile-OSu (52.6 g) in THF (184 ml), and the mixture solution was stirred for 48 hours at room temperature. THF was evaporated under reduced pressure. The residual aqueous solution was washed with ethyl acetate, and the pH of the aqueous phase was adjusted to 2.8 by use of 2N-HCl. The aqueous phase was taken up with ethyl acetate, and the ethyl acetate layer was washed with water and dried over anhydrous sodium sulfate. Anhydrous sodium sulfate was discarded by filtration, and the filtrate was concentrated under reduced pressure and brought to dryness. The resultant gelatinous substance was solidified using a mixture of ethyl acetate and hexane (yield: 53.0 g (86%)).

The obtained Boc-Ile-Gln-OH (53.0 g) was dissolved in DMF (271 ml). To the resultant solution were added HOSu (17.0 g) and DCC (30.4 g), and the mixture was stirred for 4 hours at a temperature not higher than 10° C. The precipitation was removed by filtration. The filtrate was combined with the washing and the resultant DMF solution (volume of DMF: 430 ml) was used in the subsequent step.

Asparagine (23.2 g; by K.K. Peptide Kenkyusho) was suspended in pure water (590 ml), and the suspension was dissolved by the addition of triethylamine (18.6 g). The solution was cooled at a temperature not higher than 5° C. The DMF solution previously prepared was added dropwise. The mixture was stirred at the above temperature for 12 hours, and then concentrated and dried under reduced pressure. The residue was dissolved in 5 wt. % of aqueous sodium hydrogencarbonate solution (214 ml), and the resultant solution was washed with ethyl acetate. The pH of the aqueous phase was adjusted to 2.8 by use of 2N-HCl. The aqueous phase was then allowed to stand for 24 hours at 4° C. The precipitation was collected by filtration, brought to dryness, and recrystallized with hydrated ethanol, to thereby obtain compound (4) (yield 38.0 g).

Melting point: 225–227° C.(decomposition)

[α]$_D$–45.7° (1 wt./vol. % in 0.1N-NaOH)

Synthesis Example 3:

Synthesis of 4-[4-(4-methoxyphenylmethyl)thio] thianylacetic acid (compound (7): corresponding to compound (XI) in which protective group R$^3$ is MBzl)

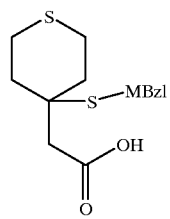

(7)

1) First, ethyl-4-thianilidene acetate was synthesized.

Ethyl diethylphosphonoacetate (88.0 g; by Wako Pure Chemical Industries, Ltd.) was added dropwise to a suspension of sodium hydride (60 wt. % oily substance) (15.0 g) in toluene (100 ml) while the temperature was controlled to be 20° C. or less. The mixture was stirred for 1 hour at room temperature to thereby obtain a pale yellow transparent solution.

This solution was added dropwise to a suspension of tetrahydrothiopyran-4-one (43.5 g, by Wako Pure Chemical Industries, Ltd.) in toluene (200 ml) while the temperature was controlled to be 10° C. or less. After completion of addition, the mixture was stirred for an additional 1 hour, and subsequently, water (200 ml) was added to the reaction mixture, followed by partitioning.

The aqueous layer was further taken up with toluene (100 ml), and the toluene layers was combined, washed with a saturated NaCl aqueous solution, and dried over anhydrous magnesium sulfate. The desiccant was discarded by filtration, and toluene was evaporated under reduced pressure. The obtained oily substance was distilled under reduced pressure (94° C., 533 Pa) so as to afford ethyl-4-thianilidene acetate (yield: 65.6 g (94%)).

2) Subsequently, ethyl-4-[4-(4-methoxyphenylmethyl) thio]thianylacetate was synthesized through use of the compound obtained in step 1).

A mixture of ethyl 4-thianilidene acetate (60 g) and 4-methoxybenzylmercaptane (90% purity; by Wako Pure Chemical Industries, Ltd.) (57.9 g) was cooled on ice. Sodium methoxide (28 wt. % methanol solution) (1.2 ml) was added to the mixture. The mixture was stirred for 4.5 hours in a nitrogen atmosphere at room temperature. Acetic acid (0.4 ml), and then diisopropyl ether (200 ml) and the same volume of saturated brine were added to the reaction mixture. Diisopropyl ether layer was separated, washed with a small amount of saturated brine, and dried over anhydrous magnesium sulfate. The desiccant was discarded by filtration, and the solvent was evaporated under reduced pressure so as to afford an oily substance (yield 103 g (94%)).

3) In the final step, 4-[4-(4-methoxyphenylmethyl)thio] thianylacetic acid was synthesized.

To a suspension of ethyl 4-[4-(4-methoxyphenylmethyl) thio]thianyl acetate (103 g) in methanol (400 ml) was added a solution of potassium carbonate (250 g) in water (200 ml). The mixture was refluxed with heat while being vigorously stirred for 8 hours at a bath temperature of 80–90° C. in a nitrogen atmosphere. After completion of reaction, the reaction was allowed to cool. Water (250 ml) was added, and methanol was evaporated under reduced pressure. Water (500 ml) was further added to the residual aqueous solution, followed by washing twice with diisopropyl ether (150 ml). Conc. HCl (ca. 300 ml) was added to the aqueous phase for adjusting the pH to 1–2. The crystals that precipitated were taken up with diethyl ether, and the solvent was evaporated. The resultant crystals were recrystallized with a mixture of ethyl acetate and hexane, to thereby obtain compound (7) having a melting point of 110° C. (yield: 73.2 g (77%)).

Example 1

Synthesis of compound (8) (which corresponds to a hydrochloric acid salt of compound (II) in which protective group $R^1$ is formyl and $R^2$ is a hydrogen atom)

FAB-MS revealed that m/z was 679 (M+1).

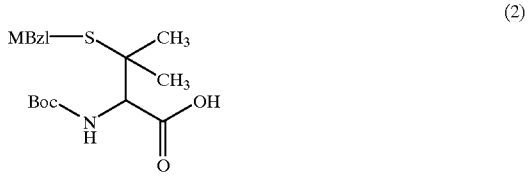
(2)

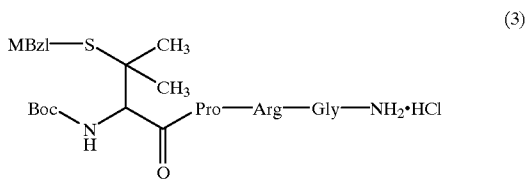
(3)

2) Synthesis of compound (5) (which corresponds to a hydrochloric acid salt of compound (VIII) in which $R^2$ is a hydrogen atom, protective group $R^3$ is MBzl, and protective group $R^6$ is Boc).

Compound (3) (45.7 g) was dissolved in TFA (150 ml) at a temperature not higher than 5° C., and the solution was stirred for 1 hour. TFA was evaporated under reduced pressure, to thereby afford an oily material. To the resultant oily material was added a solution (64 ml) obtained by

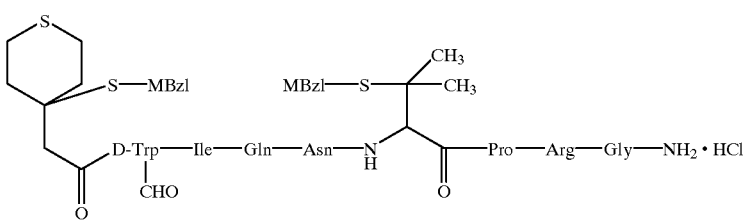
(8)

1) Compound (1) (41.5 g) obtained in Synthesis Example 1 was dissolved in methanol (170 ml). 10 wt. %) of Pd/C (2.1 g) was added to the solution. Hydrogen gas was then run through the solution with stirring until the raw material was undetected. Pd/C was discarded by filtration, and the filtrate was concentrated under reduced pressure so as to afford an oily material.

The resultant oily material was dissolved in DMF (170 ml). To the resultant solution were added compound (2) (31.7 g; by Watanabe Kagaku Kogyo K.K.) and HOBt.H$_2$O (13.2 g) The solution was cooled to a temperature of not higher than 10° C. DCC (17.7 g) was added. The mixture was stirred for 24 hours at room temperature. The white precipitation was removed by filtration and the filtrate was concentrated under reduced pressure so as to obtain an oily material. Ethyl acetate was added to the residue for solidification. The solidified materials were thoroughly washed with ethyl acetate, to thereby obtain 46.5 g of compound (3) (yield 77%). The amino acid composition (acid decomposition) of compound (3) was as follows:

Gly: 1.04 (1), Arg: 1.02 (1), Pro: 0.94 (1).

dissolving 4N equivalent HCl gas in DOX (i.e., 4N-HCl/ DOX; by Wako Pure Chemical Industries, Ltd.). Isopropylether (183 ml) was also added for solidification.

The solidified materials were collected by filtration, washed thoroughly with isopropyl ether, and dried under reduced pressure. The dry material was dissolved in NMP (440 ml). The solution was neutralized with N-methylmorpholine (NMM) to fall in the pH range of 8–9. Boc-Ile-Gln-Asn-OH (compound (4)) (30.3 g) obtained in Synthesis Example 2, and then HOOBt (13.6 g; by Kokusan Kagaku K.K.) were added. The mixture was cooled at a temperature of −10° C. or below, and a hydrochloric acid salt of WSC (WSC.HCl; by K.K. Peptide Kenkyusho) (12.3 g) was added. The mixture was stirred at the above temperature for 24 hours. The precipitation was removed by filtration, and the filtrate was concentrated and dried under reduced pressure. Ethyl acetate was added to the residue, and the solidified materials were collected by filtration, followed by thorough washing with ethyl acetate. The collected material was subjected to a reprecipitation procedure by use of isopropyl alcohol and isopropyl ether. The resultant materials were collected by filtration, to thereby obtain 65.9 g of compound (5) (yield 96%). The amino acid composition (acid decomposition) of compound (5) was as follows:

Asp: 0.85 (1), Glu: 0.92 (1), Gly: 1.11 (1), Ile: 0.99 (1), Arg: 1.13 (1), Pro: 1.00 (1).

FAB-MS revealed that m/z was 1035 (M+1).

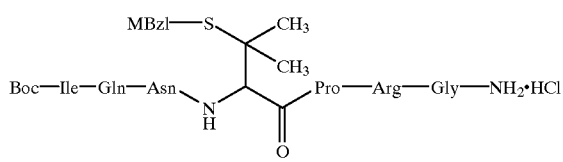

(5)

3) Synthesis of compound (6) (which corresponds to a hydrochloric acid salt of compound (X) in which protective group $R^1$ is formyl, $R^2$ is a hydrogen atom, protective group $R^3$ is MBzl, and protective group $R^7$ is Boc).

Compound (5) (73.9 g) was dissolved in TFA (293 ml) at a temperature not higher than 5° C., and the solution was stirred for 1 hour. TFA was evaporated under reduced pressure, to thereby afford an oily material. To the residue was added 4N-HCl/DOX (69 ml). Isopropylether (293 ml) was also added so as to solidify.

The solidified substance was collected by filtration, washed thoroughly with isopropyl ether, and dried under reduced pressure. The dry material was dissolved in DMF (391 ml). The solution was neutralized with NMM to fall in the pH range of 8–9. Boc-D-Trp(-CHO)-OH (22.9 g; by K.K. Peptide kenkyusho), and then HOBt (10.6 g) were added. The mixture was cooled at a temperature of 5° C. or below, and DCC (14.3 g) was added. The mixture was stirred at room temperature for 24 hours. The precipitation was discarded by filtration, and the filtrate was concentrated and dried under reduced pressure. Ethyl acetate was added to the residue, and the solidified materials were collected by filtration, followed by thorough washing with ethyl acetate. The collected material was dispersed in isopropyl alcohol, and the resultant suspension was sufficiently cooled. The dispersed materials were collected by filtration, to thereby obtain 80.3 g of compound (6) (yield 90.6%). The amino acid composition (acid decomposition) of compound (6) was as follows:

Asp: 0.92 (1), Glu: 0.98 (1), Gly: 1.12 (1), Ile: 0.84 (1), Arg: 1.11 (1), Pro: 1.03 (1).

FAB-MS revealed that m/z was 1249 (M+l).

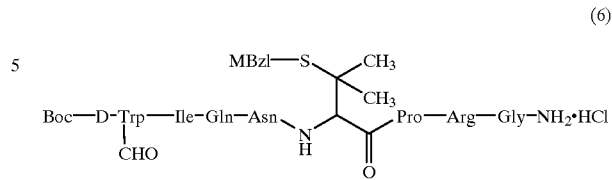

(6)

4) Synthesis of compound (8) (which corresponds to a hydrochloric acid salt of compound (II) in which protective group $R^1$ is formyl and $R^2$ is a hydrogen atom)

Compound (6) (79.7 g) was dissolved in TFA (225 ml) at a temperature not higher than 5° C., and the solution was stirred for 2 hours. TFA was evaporated under reduced pressure. 4N-HCl/DOX (62 ml) was added to the resultant oily material. Isopropyl ether (225 ml) was added so as to solidify.

The solidified substance was collected by filtration, washed thoroughly with isopropyl ether, and dried under reduced pressure. The dry material was dissolved in DMF (328 ml). The solution was neutralized with NMM to fall in the pH range of 8–9. Compound (7) (19.4 g) obtained in Synthesis Example 3, and then HOBt (9.5 g) were added. The mixture was cooled at 5° C. or below, and DCC (12.8 g) was added. The mixture was stirred at room temperature for 24 hours. The precipitation was discarded by filtration, and the filtrate was concentrated and dried under reduced pressure. Ethyl acetate was added to the residue, and the solidified materials were collected by filtration, followed by thorough washing with ethyl acetate. The collected material was dispersed in isopropyl alcohol, to thereby obtain 85.5 g of compound (8) (yield 93.2%). The amino acid composition (acid decomposition) of compound (8) was as follows:

Asp: 0.90 (1), Glu: 0.91 (1), Gly: 1.10 (1), Ile: 0.96 (1), Arg: 1.10 (1), Pro: 1.03 (1).

FAB-MS revealed that m/z was 1443 (M+1).

Example 2

Synthesis of compound (11) (which corresponds to a hydrochloric acid salt of compound (I))

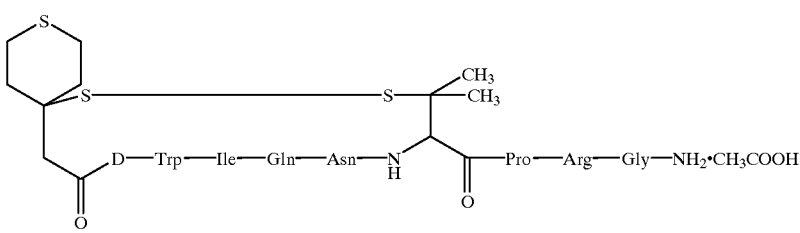

(11)

1) Compound (8) (85.0 g) and m-cresol (45.0 g) were dissolved in TFA (350 ml) at a temperature of not higher than 10° C. Methanesulfonic acid (21.6 ml) was added to the solution, and the mixture was stirred for 3 hours at room temperature. To the reaction mixture was added hexane (2000 ml) containing 1.1 wt. % of dichloromethane, and the resultant mixture was stirred sufficiently. The hexane layer was discarded, to thereby obtain an oily material containing compound (9).

2) The oily material was dissolved in ammonium acetate buffer aqueous solution (28.6 liters; pH 5.0). Ammonium acetate buffer solution (28.6 liters; pH 5.0) in which potassium ferricyanide (22.7 g) had been dissolved was added. The mixture was stirred for 24 hours at room temperature so as to form intramolecular SS bonds, to thereby obtain compound (10).

3) Subsequently, without separating compound (10), potassium ferricyanide remaining in the reaction mixture and potassium ferrocyanide resulting from the reaction were removed by use of an anion-exchange resin. The pH of the reaction mixture was adjusted to 9.5 with 28 wt. % ammonia water, and the mixture was stirred for 24 hours.

The reaction mixture was passed through a column packed with reversed phase silica gel so as to have compound (10) adsorbed thereon, followed by elution with an aqueous solution containing 60 wt. % acetonitrile. Acetonitrile was distilled off under reduced pressure, to thereby obtain an aqueous solution containing compound (11).

4) The aqueous solution containing compound (11) was adsorbed onto type CM ion exchange resin (weakly acidic cation-exchange resin) placed in a column, followed by elution with ammonium acetate buffer, to thereby obtain an acetic acid addition salt of compound (11). The yield was 30.0 g (42.3%).

to have pH 4.0, 5.0, 6.0, 7.0, or 8.0 by use of acetic acid or ammonia water.

To each of the solutions having different pHs and containing compound (9), a potassium ferricyanide solution was added dropwise, and the mixture was stirred for 24 hours at room temperature. The conversion rates at respective pHs were normalized with respect to the conversion rate at pH 7.0 and evaluated. The results are shown in Table 1. Also, the relation between the pH of the reaction mixture and the relative conversion rate is shown in FIG. 1. From FIG. 1, it is clear that the conversion rate was high about pH 5.

TABLE 1

| pH of Reaction Mixture | Relative Conversion rate |
| --- | --- |
| 8.0 | 0.88 |
| 7.0 | 1.00 |
| 6.0 | 1.12 |
| 5.0 | 1.26 |
| 4.0 | 0.89 |

In the present invention, compound (I) is prepared by use of a compound having MBzl groups as the protective groups for the thiol groups. Therefore, strong acid is not required for removing the protective groups. Also, the method of the invention facilitates industrial production.

Moreover, intramolecular SS bonds can be formed under very mild conditions of pH 4.0–6.0, while the formation of intermolecular SS bonds is suppressed and intramolecular cyclization becomes dominant. Thus, side reactions can also be suppressed, and compound (I) can be obtained at high yield.

During the synthesis of compound (I), the present invention does not require a cleavage step of peptide resins as required in the solid phase method. Thus, there is no chance

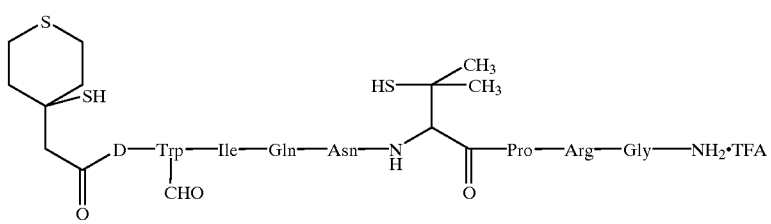

(9)

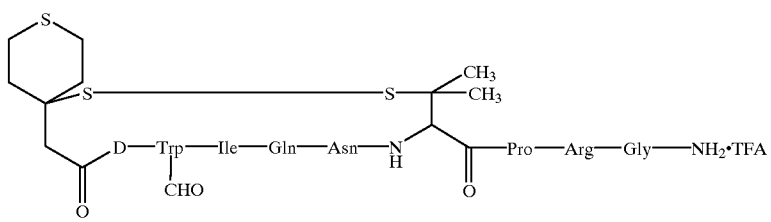

(10)

Reference Example

The effect of pH on the formation of intramolecular SS bonds of compound (9) was investigated.

The compound (9) prepared in Example 2 was dissolved in 40 mM ammonium acetate buffer so that the concentration of compound (9) became 2 mM/liter. The pH of the solution was adjusted to 4.0, 5.0, 6.0, 7.0, or 8.0 by use of acetic acid or ammonia water.

In the meantime, potassium ferricyanide solutions (2 mM/liter, 40 mM ammonium acetate buffer) were prepared for compound (I) to be contaminated with impurities migrated from resins. Since a backbone synthesis method is used making use of a fragment condensation method, lacking of amino acid is prevented, to thereby enable preparation of compound (I) having a high level of purity.

Thus, according to the present invention, a peptide derivative, compound (I), having pharmaceutical activities such as prevention of early stage abortion can be obtained at high purity and high yield, and also industrially prepared with high efficiency.

What is claimed is:

1. A method for preparing a peptide derivative of formula (I) or a salt thereof:

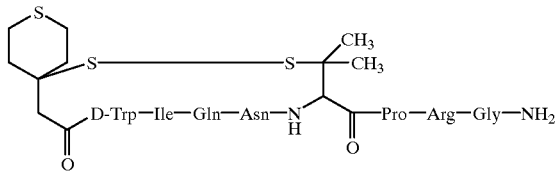
(I)

including the steps of:

removing two MBzl groups from a compound of formula (II) or a salt thereof: wherein the compound (II) or the salt thereof is reacted with a mixture of phenols, trifluoroacetic acid, and methane-sulfonic acid at a temperature between 0 and 30° C.,

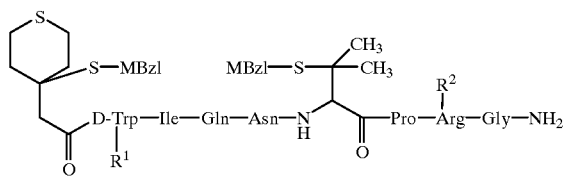
(II)

and MBzl represents a 4-methoxybenzyl group which serves as a protective group for a thiol group, $R^1$ represents a hydrogen atom or a protective group for an indolyl group of D-Trp;

and subsequently oxidizing in an aqueous buffer solution having a pH from 4.0 to 5.0 to form an intramolecular disulphide bond.

2. A method according to claim 1, wherein the intramolecular disulphide bond is formed by oxidation using potassium ferricyanide.

3. A method according to claim 1, wherein the intramolecular disulphide bond is formed by oxidation and subsequently a protective group $R^1$ is removed.

4. A method according to claim 1, wherein $R^1$ is a formyl group, and the formyl group is removed after formation of the intramolecular disulphide bond.

5. A method according to claim 1, wherein $R^1$ is a formyl group, and the formyl group and the two MBzl groups are removed from the compound of formula (II), and subsequently the intramolecular disulphide bond is formed.

6. A method according to claim 1, wherein $R^1$ of the compound of formula (II) is a hydrogen atom.

* * * * *